United States Patent
Dubois

(10) Patent No.: US 8,378,136 B2
(45) Date of Patent: Feb. 19, 2013

(54) PROCESS FOR MANUFACTURING ACROLEIN FROM GLYCEROL

(75) Inventor: Jean-Luc Dubois, Millery (FR)

(73) Assignee: Arkema France, Colombes (FR)

(*) Notice: Subject to any disclaimer, the term of this patent is extended or adjusted under 35 U.S.C. 154(b) by 113 days.

(21) Appl. No.: 13/125,475

(22) PCT Filed: Oct. 5, 2009

(86) PCT No.: PCT/EP2009/062897
§ 371 (c)(1), (2), (4) Date: Apr. 21, 2011

(87) PCT Pub. No.: WO2010/046227
PCT Pub. Date: Apr. 29, 2010

(65) Prior Publication Data
US 2011/0213174 A1 Sep. 1, 2011

(30) Foreign Application Priority Data
Oct. 24, 2008 (EP) .................................. 08167478

(51) Int. Cl.
*C07C 45/52* (2006.01)
*C07C 253/26* (2006.01)
*C07C 51/16* (2006.01)

(52) U.S. Cl. ........ 558/315; 562/532; 562/533; 562/535; 568/486

(58) Field of Classification Search .................. None
See application file for complete search history.

(56) References Cited

U.S. PATENT DOCUMENTS

| 2,558,520 | A | * | 6/1951 | Hoyt et al. | 568/486 |
| 3,925,464 | A | * | 12/1975 | Oda et al. | 562/535 |
| 5,387,720 | A | * | 2/1995 | Neher et al. | 568/486 |
| 5,426,249 | A | * | 6/1995 | Haas et al. | 568/862 |
| 7,396,962 | B1 | * | 7/2008 | Dubois et al. | 568/485 |
| 7,531,699 | B2 | * | 5/2009 | Dubois | 568/476 |
| 7,655,818 | B2 | * | 2/2010 | Dubois et al. | 568/485 |
| 8,143,454 | B2 | * | 3/2012 | Dubois | 568/465 |
| 2010/0204502 | A1 | * | 8/2010 | Dubois | 558/315 |

FOREIGN PATENT DOCUMENTS

| CN | 101225039 | * | 7/2008 |
| FR | 2882052 | * | 8/2006 |
| WO | WO 2008/052993 | * | 5/2008 |

OTHER PUBLICATIONS

Yamamoto, Naoki et al., "Thin-Layered Sheets of VOHPO4.0.5H2O Prepared from VOPO4.2H2O by Intercalation-Exfoliation-Reduction in Alcohol", Chem. Mater., 14(9), 3882-3888, 2002.*

* cited by examiner

*Primary Examiner* — Fiona T Powers
(74) *Attorney, Agent, or Firm* — Lynn B. Morreale

(57) ABSTRACT

The subject of the present invention is a process for preparing acrolein by dehydration of glycerol in the presence of a catalyst system comprising oxygen, phosphorus and at least one metal chosen from vanadium, boron or aluminium. The process is preferably carried out in the gas phase in the presence of oxygen starting from aqueous solutions of glycerol.

12 Claims, 1 Drawing Sheet

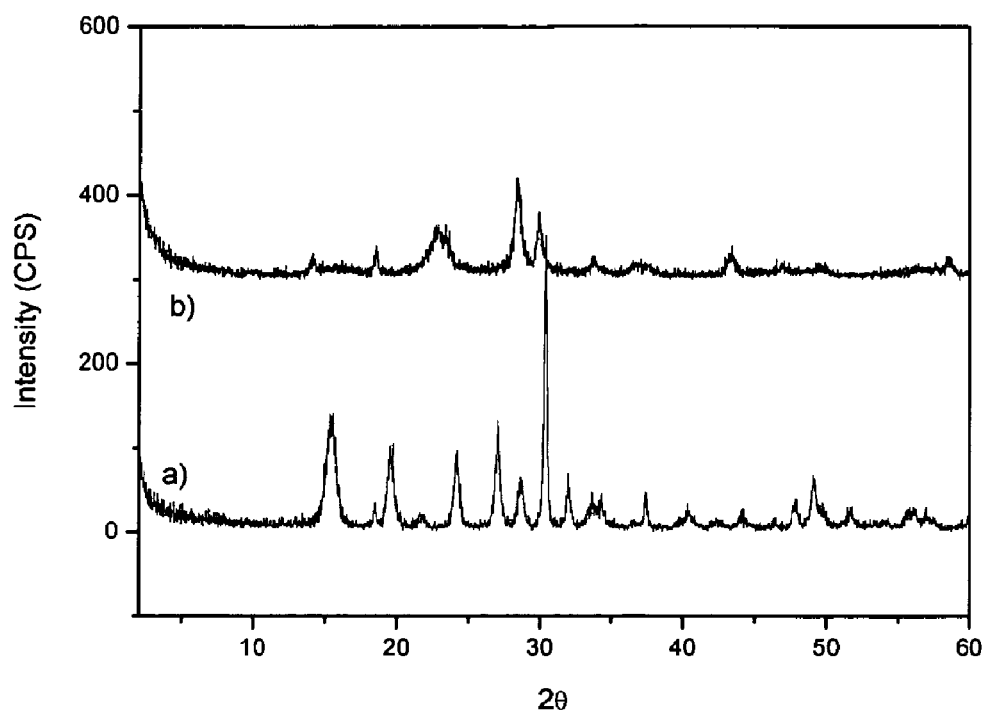
Diffractograms
a) catalyst before calcination
b) catalyst after calcination.

US 8,378,136 B2

PROCESS FOR MANUFACTURING ACROLEIN FROM GLYCEROL

CROSS-REFERENCE TO RELATED APPLICATIONS

This application is a national stage application under 35 U.S.C.§371 of PCT/EP2009/062897, filed Oct. 5,2009, which claims benefit to European application EP 08167478.0, filed on Oct 24, 2008, all of which are hereby incorated by reference.

FIELD OF THE INVENTION

The present invention relates to the production of acrolein and/or acrylic acid from glycerol and, more particularly, one subject of the present invention is a process for preparing acrolein by dehydration of glycerol in the presence of a catalyst system based on a mixed oxide of phosphorus and on at least one metal chosen from vanadium, boron or aluminium.

BACKGROUND OF THE INVENTION

Fossil resources, such as oil cuts, for the chemical industry will be exhausted in a few decades. Resources of natural and renewable origin such as alternative raw materials are consequently being studied more and more.

Acrolein is a key intermediate for the synthesis of methionine, a synthetic protein used as an animal feed supplement, which has emerged as a substitute for fishmeal. Acrolein is also a non-isolated synthetic intermediate of acrylic acid, for which the importance of its applications and its derivatives is known. Acrolein also leads, via reaction with methyl vinyl ether then hydrolysis, to glutaraldehyde, which has many uses in leather tanning, as a biocide in oil well drilling and during the treatment of cutting oils, and as a chemical sterilising agent and disinfectant for hospital equipment.

Acrolein is produced industrially by oxidation, in the gas phase, of propylene via the oxygen in the air in the presence of catalyst systems based on mixed oxides. Glycerol, derived from plant oils in the production of biodiesel fuels is one of the routes envisaged as a substitute for propylene, glycerol being able to be subjected to a catalytic dehydration reaction in order to produce acrolein. Such a process makes it possible to thus respond to the concept of green chemistry within a more general context of protecting the environment.

Numerous catalyst systems have already been the subject of studies for the dehydration reaction of glycerol to acrolein.

A process is known from Patent FR 695 931 for preparing acrolein from glycerol according to which acid salts having at least three acid functional groups or mixtures of these salts are used as catalysts. The preparation of these catalysts consists in impregnating, for example with iron phosphate, pumice that has been reduced to pea-sized fragments. According to the teaching of the patent, the yield obtained with this type of catalyst is greater than 80%.

In U.S. Pat. No. 2,558,520, the dehydration reaction is carried out in gas/liquid phase in the presence of diatomaceous earths impregnated with phosphoric acid salts, in suspension in an aromatic solvent. A degree of conversion of glycerol to acrolein of 72.3% is obtained under these conditions.

U.S. Pat. No. 5,387,720 describes a process for producing acrolein by dehydration of glycerol, in liquid phase or in gas phase, at a temperature ranging up to 340° C., over solid acid catalysts that are defined by their Hammett acidity. The catalysts must have a Hammett acidity below +2 and preferably below −3. These catalysts correspond, for example, to natural or synthetic siliceous materials such as mordenite, montmorillonite or acidic zeolites; supports, such as oxides or siliceous materials, for example alumina ($Al_2O_3$) or titanium oxide ($TiO_2$) covered by monobasic, dibasic or tribasic inorganic acids; oxides or mixed oxides such as gamma-alumina, $ZnO/Al_2O_3$ mixed oxide, or else heteropolyacids. The use of these catalysts will make it possible to solve the problem of formation of secondary products generated with the iron phosphate type catalysts described in the aforementioned document FR 695 931.

According to Application WO 2006/087084, the strongly acidic solid catalysts for which the Hammett acidity $H_0$ is between −9 and −18, have a strong catalytic activity for the dehydration reaction of glycerol to acrolein and are deactivated less quickly.

EP 2 006 273 discloses a process for production of acrolein from glycerol using aluminium phosphates with different aluminium to phosphorous ratios; the presence of an supplemental element in the structure of these catalysts is not contemplated.

Alumina impregnated by phosphoric acid are already known by FR 2 882 052 for the reaction of dehydration of glycerol, but rapid deactivation is observed for these catalysts.

However, the catalysts recommended in the prior art for producing acrolein from glycerol generally lead to formation of by-products such as hydroxypropanone, propanaldehyde, acetaldehyde, acetone, addition products of acrolein to glycerol, polycondensation products of glycerol, cyclic glycerol ethers, but also phenol and polyaromatic compounds that originate from the formation of coke on the catalyst and therefore from its deactivation. The presence of by-products in acrolein, especially propanaldehyde or propionic acid, poses numerous problems for the separation of acrolein and requires separation and purification steps that result in high costs for the recovery of purified acrolein. Furthermore, when acrolein is used for producing acrylic acid, the propanaldehyde present may be oxidized to propionic acid which is difficult to separate from acrylic acid, especially by distillation. These impurities that are present greatly reduce the field of application of the acrolein produced by dehydration of glycerol.

The Applicant Company has therefore sought to improve the production of acrolein from glycerol using more selective catalysts that make it possible to obtain high yields of acrolein and that have an activity over long periods.

In the field of catalysts, the use of catalyst systems based on iron phosphate has been widely described, these catalysts being particularly suitable for the oxydehydrogenation of saturated carboxylic acids to unsaturated carboxylic acids, in particular the conversion of isobutyric acid to methacrylic acid (FR 2,514,756; FR 2,497,795; FR 245,604; U.S. Pat. No. 4,364,856; FR 2,657,792; FR 2,498,475), or for the oxydehydrogenation of saturated aldehydes to unsaturated aldehydes and more specifically for the production of methacrolein from isobutaraldehyde (U.S. Pat. No. 4,381,411).

Mixed vanadium-phosphorus oxides are well known as catalysts for the selective oxidation of butane to maleic anhydride. The P/V atomic ratio of the active structure of these catalysts is generally between 1.2 and 2.0. Catalysts based on phosphorus and on vanadium with a P/V ratio between 1.0 and 1.2 have been found to be very effective, moreover, for the selective oxidation of butane to maleic anhydride (Bull. Chem. Soc. Jpn, 58, 2163-2171 (1985)).

The structure and the role of phosphorus in mixed V/P catalysts and also the reaction mechanisms used have been the subject of numerous studies. Among the active phases, mention may be made of $VOHPO_4.0.5H_2O$; $VOPO_4$; $VOPO_4.2H_2O$; $(VO)_2P_2O_7$; $VO(H_2PO_4)_2$; $VO(PO_3)_2$. Various modes for preparing these catalysts may be used, among which mention may be made of:

- a first mode consists in preparing a precursor, generally from vanadium oxide $V_2O_5$ and an acid solution such as, for example, oxalic acid, ammonium hydrogen phosphate or phosphoric acid. A precipitate is formed, which is then filtered, washed and dried. These precursors are then calcined under oxygen, nitrogen or air at a temperature generally between 450° C. and 600° C. (Okuhara et al., Bull. Chem. Soc. Jpn, 58, 2163-2171 (1985));
- a second preparation mode is based on the preparation of the precursor $VOHPO_4.0.5H_2O$, then its thermal conversion to a vanadium pyrophosphate $(VO)_2P_2O_7$ active phase (E. Bordes et al., Journal of Solid State Chemistry 55, 270-279 (1984); J. Johnson et al., J. Am. Chem. Soc. (1984), 106, 8123-8128); Busca et al., Journal of Catalysis, 99, 400-414 (1986));
- a third preparation mode, which has been widely studied, is based on the preparation of the precursor $VOPO_4.2H_2O$, then its reduction with a primary or secondary alcohol such as, for example, 1-butanol, 2-butanol, isobutanol, pentanol, 2-pentanol, 1-, 2- or 3-hexanol, 1-, 2- or 3-heptanol, 1-, 2- or 3-octanol, nonanol, decanol, etc. (Hutchings et al., Catalysis Today, 33, (1997), 161-171); J. Chem. Soc. Chem. Commun. 1994, 1093-1094; J. Chem. Soc. Faraday Trans. 1996, 92(1), 137-142; Chemistry letters 2001, 184-485; Chem. Mater 2002, 14, 3882-3888).

The catalytic activity of these various phases has been studied in the oxidation reactions of butane, of butene or of butadiene to maleic anhydride (G. Centi New developments in Selective Oxidation, 1990, Elsevier Science Publishers, B.V. Amsterdam, 605-615).

Other applications have also been found for mixed vanadium/phosphate oxides such as the ammoxidation of propane (G. Centi et al., J. Catal; 142 (1993), 70), the oxidation of pentane to phthalic anhydride (G. Centi et al., Sci. Technol. 1 (1995) 225). But these catalysts, just like other mixed oxides such as boron/phosphate or aluminium/phosphate, have never been the subject of studies for the dehydration reaction of glycerol to acrolein.

The Applicant Company has now found that systems based on a mixed oxide of phosphorus and on at least one metal chosen from vanadium, boron or aluminium have a high-performance catalytic activity for the dehydration of glycerol to acrolein while overcoming the drawbacks of the existing catalysts for this reaction.

SUMMARY OF THE INVENTION

One subject of the present invention is therefore a process for manufacturing acrolein from glycerol wherein the dehydration reaction of glycerol is carried out in the presence of a catalyst system comprising oxygen, phosphorus, and at least one metal M chosen from vanadium, boron or aluminium.

The catalyst system comprises, as a main constituent, a catalyst corresponding to the general formula

in which:
M represents V, B or Al;
M' represents an element selected from hydrogen atom or elements belonging to Group 1 to Group 16 of the Periodic Table;
x ranging from 0.2 to 3.0, limits included, preferably ranging from 0.5 to 2.5, most preferably from 1 to 1.5;
y ranging from 0 to 2.0, limits included, preferably from 0 to 1.0; and y is different from 0 when M represents Al; and
z is the amount of oxygen bound to the other elements and that corresponds to their oxidation state.

Preferably, M represents vanadium.

Advantageously, M' represents at least one of the following elements: Cr, Mn, Fe, Ni, CO, Zr, Nb, Mo, Sb, Sn, Te, Ta, W, Bi, Ti, S, alone or as a mixture.

The elements Fe, Ni, Co, Nb, Mo, Sb, Te W, and S are preferred as the metal M'.

The catalyst in the process according to the invention may be a bulk catalyst and is, in this case, used without any support, resulting, as is, in an excellent catalytic activity.

BRIEF DESCRIPTION OF DRAWINGS

FIG. 1: Diffractograms of a) VP catalyst before calcination and b) VP catalyst after calcination.

DETAILED DESCRIPTION OF CERTAIN EMBODIMENTS OF THE INVENTION

Since the catalyst used in this invention for producing acrolein and acrylic acid for catalytic dehydration reaction of glycerin has a high activity and high selectivity, by-products such as propionaldehyde and propionic acid are formed in lower amounts than the conventional solid acid catalysts used usually in this reaction. This makes the present invention advantageous in industrial uses, because propionaldehyde and propionic acid have their boiling points of respectively 49° C. and 141° C. which are very close to boiling points of 53° C. and 141° C. respectively of the objective compounds of acrolein and acrylic acid and hence which make purification operation much difficult.

The catalyst according to the invention may also be supported on a support, the amount of support generally representing from 0 to 90%, preferably at least 5% of the total weight of the catalyst, in most cases from 5 to 90% of the total weight of the catalyst. This ratio naturally varies depending on the type of support material, taking into account that the latter must give the catalyst mechanical strength and increase its specific surface area. It is possible to use, as a support, any material such as silica, alumina, titanium oxide, silicon carbide, silica/alumina mixture, silicates, borates or carbonates on condition that these products are stable under the reaction conditions to which the catalyst will be subjected. Preferably, the support for the catalyst according to the invention consists of silica that can be used, for example, during the preparation of catalysts in the form of silica gel.

As starting compounds for obtaining the catalyst composition for the process of the present invention, use is generally made for vanadium-based compounds, of penta, tetra or tri valence vanadium compound such as vanadium pentoxide, metavanadinic acid salts and oxyhalogenated vanadium, preferably vanadium pentoxide $V_2O_5$. Use is generally made of boric acid for boron-based compounds and of an aluminium salt such as, for example, aluminium nitrate for aluminium based compounds, without however these raw materials being limiting. As phosphorus-based compounds, it is possible to use alkali metal phosphates, ammonium phosphates, and phosphoric and phosphorus acids, etc. Preferably, phosphoric acid is used. Commercially available 85 wt % phosphoric acid can be used but it is desirable to use substantially anhydrous phosphoric acid in order to produce a catalyst that can produce acrolein and acrylic acid at high yield. The substantially anhydrous is understood that the content of phosphoric acid in term of orthophosphoric acid $H_3PO_4$ is more than 95 wt %, preferably more than 98 wt %.

As compounds of other M' elements, it is possible to use, for example, oxides, halides, sulphates, salts of organic monocarboxylic or polycarboxylic acids, etc.

The catalyst may be prepared according to any method that is already known, all the preparation methods generally comprising a step of final activation of the catalyst composition, which generally consists of a calcination at a temperature between 350 and 1000° C. The calcination (firing) is carried out in an atmosphere of inert gas such as nitrogen and argon, or in air, or in a mixture of air containing reducing gas such as hydrocarbon, or in a mixed gas thereof containing further steam. A firing furnace is not limited specially and can be Muffle furnace, rotary kiln and fluidized bed firing furnace. The calcination can be carried out in a reaction tube used as a reactor. The calcination time duration is preferably 0.5 to 500 hours.

Reference may more precisely be made to the prior art documents cited previously for the P/V mixed catalysts in order to use the most suitable method for preparing the catalysts that can be used for the process of the invention.

It is thus possible to prepare the catalysts for the process according to the invention by a variation starting from the general methods described in the aforementioned documents.

In a general reaction in connection with the preparation of phosphorus-vanadium complex oxides, vanadium compound is added to a solvent and the mixture is heated to reduce vanadium. Addition of the phosphorus compound and the compound of element belonging to Group 1 to Group 16 can be done after the reduction of vanadium is advanced to some extent, or from the start of reaction so that the phosphorus compound is reacted while vanadium is reduced. The reduction of vanadium can be effected for example by heating it in an aliphatic alcohol having a carbon number of 3 to 8 and aromatic alcohol such as benzyl alcohol. Temperature of the reaction (reduction step of vanadium and a reaction step with phosphorus compound) depends on a type of solvent used and is usually 80 to 200° C. The reaction time after the addition of phosphorus compound is usually 1 to 20 hours.

After the reaction completes, a slurry containing, as active structure, mainly a crystal structure of $VOHPO_4 \cdot \frac{1}{2}H_2O$, or a slurry containing further other metals, or a slurry deposited on a support is obtained. The slurry is then subjected to evaporation to dryness, spray drying, centrifugal separation, filtration or the like to isolate a precursor. The precursor isolated is washed with a volatile organic solvent such as acetone and can be dried by suitable means.

The precursor obtained can be used as it is or is subjected to activation so as to exhibit an activity in an objective reaction, so that it can be used as catalyst in this invention. The precursor can be fired to effect further activation treatment, resulting in that a proportion of the phosphorus-vanadium complex oxide consisting mainly of $(VO)_2P_2O_7$ is advantageously increased.

One particular embodiment of the invention consists in using a catalyst obtained according to a method based on that described by Okuhara et al. in the article from Chem. Mater. 2002, 14, 3882-3888, a method which comprises the following steps:

(a) preparation of a $VOPO_4 \cdot 2H_2O$ precursor, generally from $V_2O_5$ and $H_3PO_4$;
(b) reduction of the precursor with an alcohol containing from 3 to 8 carbon atoms or an aromatic alcohol by suspending the precursor in said alcohol and heating at a temperature ranging from 70 to 90° C., then heating between 90 and 130° C. with rapid stirring until a homogeneous alcoholic solution of exfoliated reduced $VOPO_4$ is obtained;
(c) drying of the solution obtained in step (b); and
(d) recovery of the precipitate formed in step (c), washing and drying.

The purpose of heating at a temperature ranging from 70 to 90° C. in step (b) is to exfoliate the precursor, the exfoliated compound then being reduced while heating between 90 and 130° C.

As examples of the alcohol, mention may be made of 1-propanol, 2-propanol, 2-methyl-1-propanol, 1-butanol, 2-butanol, isobutanol, 1-pentanol, 2-pentanol, 3-pentanol, 1-hexanol, 2-hexanol, 3-hexanol, 1-octanol, 2-octanol, 3-octanol, benzyl alcohol, and their mixtures.

Shape of the catalyst is not limited specially and can be granule and powder. In the gas phase reaction, the catalyst is shaped into spheres, pellets, cylindrical body, hollow cylinder bodies and bars with optional adding a molding aid. Or, the catalyst is mixed with a support and other auxiliary components and is shaped into the above configurations with optional adding a molding aid. The molded catalyst has preferably, for example in case of a sphere, a particle size of 1 to 10 mm for fixed bed catalyst, and a particle size of less than 1 mm for fluidized bed catalyst.

The process according to the invention may be carried out in the gas phase or in the liquid phase, preferably in the gas phase. When the dehydration reaction is carried out in the gas phase, various process technologies may be used, namely a fixed bed process, a fluidized bed process or a circulating fluidized bed process. It is also possible to use reactors of the plate heat exchange type.

The dehydration of glycerol may also be carried out in the liquid phase in a conventional reactor for a liquid-phase reaction, but also in a catalytic distillation type reactor. Given the large difference between the boiling points of glycerol (280° C.) and acrolein (53° C.), it is also possible to envisage a liquid-phase process at a relatively low temperature that allows a continuous distillation of the acrolein produced. The reaction is permanently shifted, thus limiting the consecutive reactions on the acrolein in a continuous equilibrium-shift reactor.

The experimental conditions of the gas-phase reaction are preferably a temperature between 180° C. and 500° C., preferably between 250 and 400° C. and a pressure between 1 and 5 bar. In the liquid phase, the reaction is preferably carried out at a temperature between 150° C. and 350° C. and a pressure which may range from 3 to 70 bar.

In the process of the invention, use is generally made of an aqueous glycerol solution having a concentration ranging from 20% to 99%, preferably between 30% and 80%, by weight in the reactor.

The glycerol solution may be used in liquid form or in gaseous form, preferably in the gas phase form.

Preferably, the process according to the invention is carried out in the presence of oxygen, or an oxygen-containing gas.

One preferred embodiment of the invention will now be described. The process for preparing acrolein from glycerol consists in sending a mixture containing at least glycerol, water, oxygen or an oxygen-containing gas, and where appropriate an inert gas and/or recycle gases, in the gas phase, over the catalyst system as defined previously, maintained at a reaction temperature between 180 and 500° C.

The charge sent into the reactor may be preheated to a preheating temperature around 180° C. to 350° C.

The process is carried out at a pressure around atmospheric pressure and more precisely, preferably at a slightly higher temperature.

The amount of oxygen is chosen so as to be outside the explosive limit at any point of the installation. The molar ratio of the molecular oxygen to the glycerol is generally around 0.1 to 1.5, preferably from 0.5 to 1.0.

Another parameter lies in the concentration of glycerol in the charge. Expressed in mole percent, the concentration of glycerol varies widely from 0.1 to 20. As is common in reactions of this type, the yield of the desired product is an inverse function of the concentration. From the point of view of obtaining a reasonable flow rate combined with an acceptable yield, the concentration of glycerol in the charge is around 3 to 16 mol %. The concentration is controlled by the amount of water and of inert gas present in the feed stream. The preferred gaseous diluent is nitrogen although other gases such as carbon dioxide, helium, argon, etc. are also suitable. Of course, when the desired concentration of glycerol permits it, air represents a suitable dilute oxidant.

The contact time expressed in seconds is the ratio between the volume of the catalyst bed and the volume of the gaseous reactants conveyed per second. The average temperature and pressure conditions in a bed may vary depending on the nature of the catalyst, the nature of the catalyst bed and the size of the catalyst. In general, the contact time is from 0.1 to 20 seconds and preferably from 0.3 to 15 seconds.

The catalysts used in the process of the present invention make it possible to attain high yields of acrolein with extremely high conversion rates which may attain up to 100% glycerol in certain cases, especially in the presence of oxygen. These results are due to the fact that these catalysts have the advantage of promoting a dehydration process that progresses evenly and is easily controllable with regard to the reaction temperatures and contact times. The reactants may be introduced over the catalyst, whether the former are already completely or only partially premixed, or may be introduced individually.

The supply of various reactants, applied to a fixed-bed or to a fluidized-bed reactor may be carried out individually or already in the form of premixes. It is also possible to introduce part of the air or optionally all of the glycerol or only part of the glycerol into the bottom of the reactor and to successively supply the remaining parts of the reactant to one or more intermediate points of the catalyst bed. When the reaction is carried out according to fixed catalyst bed techniques, such beds may be obtained according to known methods by placing the catalyst in the tubes of a multitube reactor and by removing their heat of reaction using suitable fluids flowing on the outside of the tubes, these fluids possibly, for example and most generally, consisting of mixtures of molten salts. It is also possible to operate in a reactor having several adiabatic reaction stages separated by zones for cooling the reaction mixture.

According to one particular embodiment of the invention, it is possible to place, upstream of the catalyst system based on a mixed oxide of phosphorus and at least one metal chosen from V, B or Al, a first active catalyst bed, or a first reactor enabling the dehydration reaction of glycerol to acrolein to be carried out. The gaseous reaction mixture is thus sent to a first catalyst, in contact with which the dehydration reaction of glycerol is at least partially carried out generally resulting in secondary compounds such as propanaldehyde. The reaction mixture thus obtained is then in contact with the catalyst system on which the dehydration reaction of unreacted glycerol may continue at the same time as the conversion of propanaldehyde to acrolein. The first catalyst bed may operate at a lower temperature than the second catalyst bed, thus optimizing the energy balance of the process. The acrolein obtained according to this embodiment contains a minimized amount of propanaldehyde, which widens its field of application. This configuration of reactors is possible according to various technologies, for example as an adiabatic fixed bed, but also as a multitubular fixed bed, or else, for example, as a compartmentalized fluidized bed. This configuration is also possible in the case where the first reactor operates in the liquid phase and the second, containing the mixed V/P, B/P or Al/P catalyst operates in the gas phase.

It would not be outside the scope of the present invention if the process is carried out in the presence of a gas containing propylene, as described for example in Application WO 07/090,990.

The invention also relates to the use of a catalyst system comprising as a main constituent, phosphorus-vanadium complex oxides or their precursors for carrying out the dehydration reaction of glycerol to acrolein.

The invention also relates to a process for preparing acrylic acid from glycerol comprising a first step of preparing acrolein according to the process described previously, and a step of oxidizing the acrolein to acrylic acid.

The invention also relates to a process for preparing acrylic acid from glycerol comprising a first step of preparing acrolein according to the process described previously and a second step of oxidizing the acrolein to acrylic acid, in which use is made of an intermediate step of partial condensation of water and of the heavy by-products derived from the dehydration step, as is described for example in Application WO 08/087,315.

The invention also relates to a process for preparing acrylonitrile from glycerol comprising a first step of preparing acrolein according to the process described previously, and a step of ammoxidizing the acrolein to acrylonitrile.

The following examples illustrate the present invention without however limiting the scope thereof.

EXPERIMENTAL SECTION

Examples 1 to 4

In the examples, a tubular reactor formed from a Pyrex tube was used to carry out the dehydration reaction of glycerol in the gas phase at atmospheric pressure. Introduced into the reactor were between 300 and 500 mg of a catalyst to be tested, with quartz (30-50 or 50-80 mesh) so as to obtain a catalyst bed volume of 2 ml. The reactor was placed in a heated chamber maintained at the chosen reaction temperature of 280° C. The reactor was brought to the reaction temperature over 5 to 10 minutes before the reactants were introduced. The reactor was fed with a 20 wt % or 40 wt % aqueous solution of glycerol, and with nitrogen. Oxygen was also introduced in a second series of tests. The aqueous glycerol solution was vaporized in the heated chamber, then passed over the catalyst. The calculated contact time was between 0.5 and 3 s. After the reaction, the products were condensed in a trap cooled by crushed ice. Gaseous withdrawals were carried out periodically.

For each experiment, the total mass of products at the inlet and at the outlet was measured, which made it possible to carry out a mass balance. Similarly, the products formed were analysed by chromatography. Two types of analyses were carried out:

a liquid phase analysis by GC-MS chromatography (Shimadzu GC-17A+GC/MS-QP5050A) equipped with a TC-Wax capillary column from GL Science (60 m×0.25 mm; $d_f$ 0.5 μm) and Shimadzu Class-5000 software. The quantitative analysis was carried out with an external standard (2-butanol); and a gas phase analysis by GC enabling the oxygen conversion and the CO and $CO_2$ selectivity to be determined. Methane was added in a small amount into the feedstream as an internal standard gas, making it possible to quantify the light compounds such as acrolein, acetaldehyde, propanaldehyde and formaldehyde with an FID detector.

In the following examples, the conversion of glycerol and the yields are defined as follows:

Glycerol conversion (%)=(1−number of moles of glycerol remaining/number of moles of glycerol introduced)×100.

Acrolein yield (%)=number of moles of acrolein produced/number of moles of glycerol introduced× 100.

Acrolein selectivity (in %)=number of moles of acrolein formed/number of moles of glycerol having reacted×100.

All the results are expressed as molar percentages relative to the starting glycerol.

Catalysts

Boron Phosphate Catalyst (BP Catalyst)

A boron phosphate type catalyst was prepared according to the method described in Chem. Letters Vol. 34, No. 5 (2005), p. 1232-1233. A mixture of boric acid $H_3BO_3$ and phosphoric acid $H_3PO_4$ (P/B=1) was heated at 40° C. under vacuum in a rotary evaporator to obtain a solid, which was then calcined at 360° C. for 12 h.

Vanadium Phosphate Catalyst (VP Catalyst)

Use was made of a $VOHPO_4.0.5H_2O$ catalyst supplied by Prof. Okuhara from Hokkaido University, prepared according to the method described by Okuhara et al. in Chem. Mater. 2002, 14, 3882-3888 with the reduction step in 2-propanol. This catalyst was essentially identical to that described in Table 1, and FIG. 4e of the aforementioned article. The diffractogram of this solid after intercalation, exfoliation and reduction of the $VOPO_4.2H_2O$ precursor is given as a) in FIG. 1. After calcining at 550° C. for 4 hours under $N_2$, typically $(VO)_2P_2O_7$ is obtained with its characteristic X-ray diffraction lines. The catalyst tested is the calcined catalyst represented as b) in FIG. 1.

Aluminium Phosphate Catalysts (AlP-a and AlP-p Catalysts) (Comparative)

A first catalyst (AlP-a) was prepared according to the ammonia precipitation method described in Catal. Comm. 7 (2006), 745-751. A 5 wt % ammonia solution was added dropwise to a mixture comprising a 10 wt % aqueous solution of aluminium nitrate $Al(NO_3)_3.9H_2O$, and phosphoric acid $H_3PO_4$ (88% purity), until aluminium phosphate precipitated at pH 9. The precipitate was then filtered and washed with distilled water, then dried at 110° C. for 12 h and calcined at 650° C. in air for 2 h.

A second catalyst (AlP-p) was prepared according to a precipitation method derived from the precipitation/concentration method for iron phosphates described in Catal. Rev. Sci. Eng. 40 (1998) 1-38. Added to 500 ml of distilled water containing 30 mmol of $Al(NO_3)_3.9H_2O$ were 30 mmol of $H_3PO_4$ (85% purity) with stirring. The mixture was then concentrated in a rotary evaporator at 80° C. and dried in an oven at 120° C. The white powder obtained was calcined at 650° C. in air for 4 h.

These catalysts were characterized by measurement of their specific surface area and their acidic properties according to the method of ammonia temperature-programmed desorption (TPD): see Table 1.

TABLE 1

| Catalyst | Specific surface area $m^2/g$ | Ammonia (TPD) | |
|---|---|---|---|
| | | Max. desorption temp. K | Desorbed quantity μmol/g |
| BP | 5.4 | 560 | 11 |
| VP | 15.9 | 598 | 71 |
| AlP-a | 102.6 | 562 | 108 |
| AlP-p | 12.3 | 573 | 10 |

Tests

A first series of tests was carried out at 280° C. in the absence of oxygen, the molar ratio of the reactants being $N_2/H_2O$/glycerol: 46/48/6 (corresponding to a 40 wt % aqueous solution of glycerol). The results are collated in Table 2 below.

TABLE 2

| Catalyst | GHSV, $h^{-1}$ total | GHSV, $h^{-1}$ glycerol | glycerol conversion, % | Selectivity, mol % | | | | | | |
|---|---|---|---|---|---|---|---|---|---|---|
| | | | | Acrolein | HYACE | ACET | AcA | P-al | P-ol | others |
| BP | 1400 | 82 | 96 | 81 | 6.2 | 0.2 | 0.2 | 0.1 | 0.2 | 12.5 |
| VP | 2500 | 46 | 16 | 59 | 14.3 | 2.1 | 6.8 | 0.1 | 11.9 | 5.6 |
| AlP-a | 1300 | 82 | 100 | 47 | 6.9 | 1.2 | 0.6 | 0.3 | 0.7 | 42.3 |
| AlP-p | 1300 | 83 | 70 | 54 | 7.3 | 0.1 | 0.2 | 0.1 | 1.9 | 35 |

HYACE: hydroxyacetone; ACET: acetone; AcA: acetic acid; P-al: propanaldehyde; P-ol: 2-propene-1-ol; others: formaldehyde, hydroxyacetaldehyde, phenol, formic acid, acrylic acid, cyclic ethers.

A high conversion is observed in the case of boron phosphate and aluminium phosphate and also a high acrolein selectivity is observed in the case of the boron phosphate and vanadium phosphate. These two phosphates are also distinguished by a low propanaldehyde selectivity.

The performances of the BP and VP catalysts for the dehydration reaction of a 40 wt % aqueous solution of glycerol in the presence of oxygen appear in Table 3.

TABLE 3

| Catalyst | BP | VP |
|---|---|---|
| Temperature, ° C. | 282 | 280 |
| GHSV, $h^{-1}$ | 2000 | 330 |
| Contact time, s | 1.8 | 10.9 |
| $O_2$/glycerol (moles) | 2.6 | 1 |
| Glycerol conversion, % | 100 | 100 |
| $O_2$ conversion, % | 3.6 | 70.8 |

TABLE 3-continued

| Catalyst | BP | VP |
|---|---|---|
| Yields, % | | |
| Acrolein | 65 | 79.8 |
| Acetaldehyde | 0.7 | 3.0 |
| Hydroxyacetone | 7.8 | 0.1 |
| Propanaldehyde | 0.4 | 0.0 |
| Acrylic acid | 2.4 | 0.5 |
| Acetic acid | 1.1 | 2.5 |
| CO | 0.0 | 3.9 |
| $CO_2$ | 0.5 | 8.2 |
| Others | 0 | 6.0 |

It is observed that the vanadium phosphate catalyst exceptionally results in low propanaldehyde contents, while resulting in a very high yield of acrolein.

Comparative Example 1

Two catalysts, a sulphated zirconia (90% $ZrO_2$-10% $SO_4$) from Daiichi Kigenso (supplier reference H1416) and a tungstated zirconia (90.7% $ZrO_2$-9.3% $WO_3$) from Daiichi Kigenso (supplier reference H1417) were tested by way of reference. For these tests, 10 ml of catalyst were used. The reactor was fed with a 20 wt % aqueous solution of glycerol with an average feed flow rate of 12 ml/h, and with a flow rate of 0.8 l/h of molecular oxygen. The relative $O_2$/vaporized glycerol/water vapour ratio was 6/4.5/89.5. The aqueous glycerol solution was vaporized in a heated chamber at 300° C., then passed over the catalyst. The calculated contact time was around 2.9 s. The duration of one catalyst test was around 7 hours, which corresponds to around 80 ml of aqueous glycerol solution conveyed over the catalyst. The results are indicated in Table 4 below:

TABLE 4

| | Accummulated glycerol introduced (g) | | | | |
|---|---|---|---|---|---|
| | 9 | 18 | 27 | 21 | 33 |
| Catalyst | sulphated zirconia 16.5 g | | | tungstated zirconia 17 g | |
| Glycerol conversion | 100 | 100 | 100 | 100 | 100 |
| Acrolein yield | 42.3 | 53.8 | 52.5 | 54.9 | 53.0 |
| Acrolein selectivity | 42 | 54 | 52 | 55 | 53 |
| Hydroxypropanone yield | 0.0 | 0.0 | 0.0 | 0.0 | 0.0 |
| Acetaldehyde yield | 10.3 | 9.1 | 8.2 | 9.8 | 8.7 |
| Propanaldehyde yield | 4.9 | 3.7 | 4.0 | 2.1 | 1.4 |
| Acetone yield | 0.0 | 0.4 | 0.0 | 0.1 | 0.1 |
| Phenol yield | 0.0 | 0.0 | 0.3 | 0.0 | 0.0 |
| Material balance (mass collected/mass introduced) | 96.5 | 98.0 | 98.0 | 97.2 | 97.9 |
| Quantified product balance (assayed products/glycerol introduced) | 57.5 | 66.9 | 65.0 | 66.9 | 63.2 |

Comparative Example 2

For a comparison with the phosphorus-vanadium complex oxide, phosphoric acid alumina (1 wt % $PO_4$/99 wt % $Al_2O_3$, molar ratio P/Al-0.02) as a solid acid was evaluated. The phosphoric acid alumina was prepared by a method described in JP-A1-2005-213225. Namely, 4 g of phosphoric acid was added to 2 g of Snowtex O (product of Nissan Chemical Industries) and mixed. Into the mixture, 194 g of α-alumina and 200 ml of water were added and stirred at 80° C. The resulting white slurry was evaporated in a rotary evaporator at 80° C., and finally dried at 100° C. for 6 hours.

The resulting powder was evaluated in a fixed bed type reactor at ambient pressure. The catalyst powder was compressed, crushed and then passed through a sieve to obtain particles of 9 to 12 mesh. A SUS reaction tube of 10 mm diameter was filled with 10 cc of the catalyst particles. An aqueous solution containing 20% by weight of glycerol was passed to an evaporator heated at 300° C. at a rate of 21 g/hr by a pump. The resulting gasified glycerin gas was directly passed through the catalyst together with air. The reactor containing the catalyst was heated at 350° C. The feed stream has a composition of glycerin:oxygen:nitrogen:water=4.2 mol %:2.2 mol %:8.1 mol %:85.5 mol % and GHSV was 2445 $h^{-1}$.

Result is shown in following Table 5.

TABLE 5

| Catalytic | Reaction temperature (° C.) | Glycerin conversion ratio (%) | Acrolein yield (%) | Acrylic acid yield (%) | Propionaldehyde yield (%) | Propionic acid yield (%) |
|---|---|---|---|---|---|---|
| $H_3PO_4$/$Al_2O_3$ | 350 | 92.7 | 37.8 | 0.2 | 0.6 | 0.1 |

Example 5

A precursor of $VOHPO_4 \cdot \frac{1}{2}H_2O$ was prepared as following: Namely, 100.0 g of vanadium pentoxide ($V_2O_5$) was suspended in 1000 ml of 2-methyl-1-propanol and refluxed at 105° C. under agitation for 3 hours to reduce $V_2O_5$. In 132.0 g of 98% orthophosphoric acid powder, 250 ml of 2-methyl-1-propanol was added and dissolved under agitation at 100.

The resulting orthophosphoric acid solution (132.0 g of 98% orthophosphoric acid powder/250 ml of 2-methyl-1-propanol) was added at 100° C. gradually into a yellow solution of vanadium prepared by the heat-reflux in 2-methyl-1-propanol and heat-reflux was continued at 105° C. After 3 hours, the reflux was stopped and cooled down to ambient temperature. The resulting catalyst precursor was filtered, washed with acetone and dried in a drier at 140° C. during one night to obtain a blue white phosphorus-vanadium complex The resulting catalyst was evaluated in a fixed bed type reactor at ambient pressure. The catalyst powder was compressed, crushed and then passed through a sieve to obtain particles of 9 to 12 mesh. A reaction tube of 10 mm diameter was filled with 10 cc of the catalyst particles. An aqueous solution containing 20% by weight of glycerol was passed to an evaporator heated at 300° C. at a rate of 21 g/hr by a pump. The resulting gasified glycerin gas was directly passed through the catalyst together with air. The reactor containing the catalyst was heated at 300 to 340° C. The feed stream has a composition of glycerin:oxygen:nitrogen:water=4.2 mol %:2.2 mol %:8.1 mol %:85.5 mol % and GHSV was 2445 h$^{-1}$.

The product was collected in a condenser and the resulting condensate was analyzed quantitatively by gas chromatograph (GC-7890, DB-WAX column, product of Agilent). Each product was corrected in factor by this gas chromatograph.

Results are summarized in Table 6.

Example 6

Blue white dry powder obtained in Example 5 was fired in Muffle furnace in air atmosphere at 500° C. for 3 hours to obtain a light green phosphorus-vanadium complex oxide powder.

Reactivity of this powder was evaluated by the same method as Example 5. Results are shown in Table 6.

TABLE 6

| | Catalytic | Reaction temperature (° C.) | Glycerin conversion ratio (%) | Acrolein yield (%) | Acrylic acid yield (%) | Propion- aldehyde yield (%) | Propionic acid yield (%) |
|---|---|---|---|---|---|---|---|
| Example 5 | VPO (precursor) | 300 | 100 | 49.5 | 0.2 | 0.4 | 0.2 |
| | | 340 | 100 | 42.5 | 0.3 | 0.8 | 0.0 |
| Example 6 | VPO (after firing in air) | 300 | 100 | 54.2 | 0.2 | 0.5 | 0.1 |
| | | 340 | 100 | 38.1 | 0.0 | 1.0 | 0.0 |

Example 7

Dihydrate VOPO$_4$.2H$_2$O was prepared according to the method described by Okuhara et al. in Chem. Mater. 2002, 14, 3882-3888: A mixture of V$_2$O$_5$ (24 g), H$_3$PO$_4$ (85% wt/wt, 133 mL), and H$_2$O (577 mL) was refluxed at 115° C. for 16 h. The resulting precipitate was collected by filtration, washed with 100 mL acetone, and dried for 16 h under ambient conditions. Both X-ray diffraction patterns (XRD) and infrared (IR) examinations indicated the solid to be VOPO$_4$.2H$_2$O. A suspension of VOPO$_4$.2H$_2$O (5 g) powder in 2-butanol (50 mL) was stirred under reflux for 23 h. The resulting light-blue solid, which was confirmed as hemihydrate VOHPO$_4$.0.5H$_2$O by XRD and IR, was collected by filtration, washed with 100 mL acetone and dried for 16 h under ambient conditions. Thermal treatment of VOHPO$_4$.0.5H$_2$O (2.0 g) to give pyrophosphate phase (VO)$_2$P$_2$O$_7$ was conducted in a 40-mL nitrogen flow at a temperature of 800° C. This catalyst is designated as VPO-8.

Glycerol dehydration reaction was conducted in a vertical fix-bed reactor under atmospheric pressure. The Pyrex homemade reactor with an internal diameter of 5 mm was used. A mixture of catalyst and corundum particle (50-70 mesh), typically, 0.2 g catalyst diluted with 3.0 g corundum, was loaded in the middle section of the reactor, with quartz wool packed in both ends. A thermocouple to monitor the temperature of evaporating zone and a syringe to add aqueous glycerol were placed in a position of 10-cm higher than the top of catalyst bed. The reaction temperature was monitored by a thermocouple inserted into the middle of catalyst bed. Before reaction, the catalyst was pretreated at 300° C. for 1 h in nitrogen with a flow rate of 18 mL min$^{-1}$. Aqueous glycerol (20% wt/wt) was fed at a speed of 0.50 g h$^{-1}$ by a syringe pump. The products were collected in an ice-water cold trap directly connected to the outlet of the reactor. Approximately 0.02 g of 2-butanol as internal standard and 5 mL water to absorb products were previously loaded into the cold trap. The collected samples were quickly analyzed by means of GC-MS (Shimadzu 15A, Japan) with an auto-sampler equipped with a capillary column (GL Sciences, TC-FFAP 60 m×0.25 mm×0.5 μm) and a flame ionization detector (FID). The chromatograph column was run at a program from 110° C. to 250° C. with a ramping rate of 5° C. min$^{-1}$ and kept at 250° C. for 10 min. The gas phase was analyzed by three online GCs with two thermal conductivity detectors (TCD) and one FID detector. The analysis of gas phase allowed the quantifications of carbon oxide, carbon dioxide, acetaldehyde, acrolein and acetic acid.

Catalytic results of two reactions, with (reaction 1) and without (reaction 2) adding oxygen, are given in table 7. The composition of fed gas, nitrogen/oxygen/water/glycerol, was equal to 66.6/1.7/30.3/1.5 (reaction 1), and to 65.5/0/32.9/1.6 (reaction 2) in molar ratio.

TABLE 7

| | Reaction 1 | Reaction 2 |
|---|---|---|
| $S_{BET}$ [m$^2$ g$^{-1}$] | 10.0 | |
| NH$_3$ desorption amount [μmol g$^{-1}$] | 27.5 | |
| Glycerol conversion, % | 100 | 95.1 |
| O$_2$ conversion, % | 79.8 | |
| Carbon balance | 77.0 | 65 |
| Selectivity, % | | |
| acetaldehyde | 7.8 | 8.3 |
| acetic acid | 1.9 | n.d |
| acrolein | 64.3 | 59.5 |
| 1-propanal | 0.3 | n.d |
| hydroxyacetone | 5.5 | 11.8 |
| acrylic acid | 0.3 | n.d |
| 1,3-dioxane-5-ol | 2.4 | n.d | n.d: not determinated

With VPO-8 catalyst, the glycerol conversion reaches 100% in the presence of molecular oxygen and decreases only to 95.1% in reaction 2 without oxygen.

Example 8

Al/P/S Catalyst

AlPO$_4$ (Al/P=1) was prepared, as described in Studies in Surface Science and catalysis, Vol 31, Preparation of catalysts IV, 1987, pp 199-215, from aqueous solutions of to AlCl$_3$.6H$_2$O and H$_3$PO$_4$ (85 wt %) by precipitation with propylene oxide, followed by washing with 2-propanol and drying at 120° C. for 24 h and then calcining at 650° C. for 3 h. Sulfate anions were introduced onto the AlPO$_4$ surface by impregnation until incipient wetness with aqueous solution of (NH$_4$)$_2$SO$_4$ to obtain a catalyst comprising 3 wt % of SO$_4^{2-}$. The impregnated AlPO$_4$ was dried at 120° C. for 24 h, then calcined at 400° C. for 3 h in an electric muffle furnace and stored in a dessicator. The surface area of the Al/P/S catalyst obtained by the BET method is 46 m²·g⁻¹.

Catalytic test was carried out as described in examples 1 to 4, at 280° C. with a 40 wt % aqueous solution of glycerol, and a molar ratio O₂/glycerol equal to 1.

A glycerol conversion of 100% was obtained with an acrolein selectivity of 71% for this AlP catalyst comprising sulfur as supplemental element.

Low selectivities for the by-products were observed: 4.1% (hydroxacetone), 0.9% (acetone), 0.4% (acetic acid), 0.3% (propanaldehyde) and 1.2% 2(-propene-1-ol).

The invention claimed is:

1. A process for manufacturing acrolein from glycerol comprising the steps of:
subjecting glycerol to a dehydration reaction and forming acrolein, wherein the dehydration reaction is carried out in the presence of a catalyst system comprising a catalyst having the formula:

$MP_xM'_yO_z$ wherein:
M is selected from V, B or Al;
M' is an element selected from hydrogen or elements selected from Groups 1 to 16 of the Periodic Table;
x ranges from 0.2 to 3.0, limits included;
y ranges from 0 to 2.0, limits included, wherein when M is Al, y is not 0; and
z is the amount of oxygen bound to the other elements and that corresponds to their oxidation state.

2. w) The process of claim 1, wherein M is V.

3. The process of claim 1, wherein M' is at least one of the following elements:
Cr, Mn, Fe, Ni, Co, Zr, Nb, Mo, Sb, Sn, Te, Ta, W, Bi, Ti, S, alone or as a mixture.

4. The process of claim 3, wherein M' is selected from at least one of Fe, Ni, Co, Nb, Mo, Sb, Te, W, S or mixtures thereof.

5. The process of claim 1, wherein x ranges from 0.5 to 2.5 and/or y ranges from 0 to 1.0.

6. The process of claim 1, wherein the catalyst is supported on a support.

7. The process of claim 6, wherein the support comprises silica, alumina, titanium oxide, silicon carbide, silica/alumina mixture, silicates, borates or carbonates.

8. The process of claim 1, wherein the dehydration reaction comprises passing a mixture containing at least glycerol, water, and oxygen or an oxygen-containing gas, in the gas phase, over the catalyst system that is maintained at a reaction temperature between 180 and 500° C.

9. The process of claim 1, wherein the catalyst system comprises one or more phosphorus-vanadium complex oxides or their precursors for carrying out the dehydration reaction of glycerol to acrolein.

10. The process of claim 1, further comprising oxidizing acrolein to acrylic acid.

11. The process of claim 10, further comprising partially condensing water and heavy by-products derived from the dehydration step.

12. The process of claim 1 further comprising ammoxidizing the acrolein produced to form acrylonitrile.

* * * * *